(12) United States Patent
Schedler

(10) Patent No.: US 8,197,541 B2
(45) Date of Patent: Jun. 12, 2012

(54) ACCOMMODATIVE LENS IMPLANT, CONTROLLED BY THE CILIARY MUSCLE

(75) Inventor: Markus Schedler, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 12/578,254

(22) Filed: Oct. 13, 2009

(65) Prior Publication Data
US 2010/0030332 A1 Feb. 4, 2010

Related U.S. Application Data

(62) Division of application No. 10/569,444, filed as application No. PCT/EP2004/009501 on Aug. 25, 2004, now abandoned.

(30) Foreign Application Priority Data

Aug. 26, 2003 (DE) .................................. 103 39 266
Oct. 2, 2003 (DE) .................................. 103 46 024

(51) Int. Cl.
*A61F 2/16* (2006.01)
(52) U.S. Cl. ..................... 623/6.13; 623/6.14; 623/6.34; 623/6.37; 623/6.41
(58) Field of Classification Search ............ 623/4.1, 623/6.11, 6.13–6.15, 6.18–6.21, 6.32, 6.34–6.41, 623/6.22
See application file for complete search history.

(56) References Cited

U.S. PATENT DOCUMENTS

| | | |
|---|---|---|
| 4,253,199 A | 3/1981 | Banko |
| 4,731,078 A | 3/1988 | Stoy et al. |
| 4,822,360 A | 4/1989 | Deacon |
| 4,883,485 A * | 11/1989 | Patel .............................. 623/6.13 |
| 4,888,012 A * | 12/1989 | Horn et al. .................... 623/6.13 |
| 4,892,543 A | 1/1990 | Turley |
| 4,932,966 A | 6/1990 | Christie et al. |
| 5,203,788 A * | 4/1993 | Wiley ........................... 623/6.22 |
| 5,275,623 A | 1/1994 | Sarfarazi |
| 5,443,506 A | 8/1995 | Garabet |
| 5,628,795 A * | 5/1997 | Langerman .................... 623/4.1 |
| 5,800,533 A | 9/1998 | Eggleston et al. |
| 6,117,171 A | 9/2000 | Skottun |
| 6,217,612 B1 | 4/2001 | Woods |
| 6,280,471 B1 * | 8/2001 | Peyman et al. .............. 623/6.17 |
| 2002/0026240 A1 * | 2/2002 | Pallikaris et al. ............ 623/6.13 |
| 2003/0130732 A1 | 7/2003 | Sarfarazi |
| 2004/0034414 A1 * | 2/2004 | Aharoni ........................ 623/6.34 |
| 2004/0082994 A1 * | 4/2004 | Woods et al. ................. 623/6.34 |
| 2005/0251253 A1 * | 11/2005 | Gross ............................ 623/6.13 |

\* cited by examiner

FOREIGN PATENT DOCUMENTS

| | | |
|---|---|---|
| DE | 689 02 614 T2 | 1/1993 |
| EP | 0 356 050 | 2/1990 |
| EP | 0 793 460 | 9/1997 |

*Primary Examiner* — David Isabella
*Assistant Examiner* — Andrew Iwamaye
(74) *Attorney, Agent, or Firm* — Oblon, Spivak, McClelland, Maier & Neustadt, L.L.P.

(57) ABSTRACT

The invention relates to an accommodative lens implant controlled by the ciliary muscle, consisting of at least one or more lenses made of preferably biocompatible material and disposed on a common optical axis, the at least one lens being a component of a flexible, closed implant body that is transparent in the region of the actual lens, is engaged at its outer periphery with the ciliary muscle, and has a main axis that coincides with the visual axis, and in addition at least part of the implant body with the lens or lenses comprises a fluid filling, such that the axial position of the lens or the lens system can be altered by activation of the ciliary muscle, the implant body being inserted in the sulcus of the posterior chamber of the eye or attached to the ciliary muscle.

14 Claims, 3 Drawing Sheets

ACCOMMODATIVE LENS IMPLANT, CONTROLLED BY THE CILIARY MUSCLE

CROSS-REFERENCE TO RELATED APPLICATIONS

This application is a divisional of and is based upon and claims the benefit of priority under 35 U.S.C. §120 for U.S. Ser. No. 10/569,444, filed Jan. 31, 2007, which is a national stage of PCT/EP04/09501, filed Aug. 25, 2004, and claims the benefit of priority under 35 U.S.C. §119 from German Application Nos. 103 39 266.1, filed Aug. 26, 2003, and 103 46 024.1, filed Oct. 2, 2003, the entire contents of each which are incorporated herein by reference.

DESCRIPTION

The invention relates to a lens implant that is capable of accommodation under the control of the ciliary muscle and consists of at least one or several lenses made of a preferably biocompatible material, which are disposed on a common optical axis.

BACKGROUND

The publication EP 0 793 460 B1 discloses an accommodative artificial lens implant employing optics that move in reaction to changes in the ciliary muscle. The intraocular lens arrangement used there is intended to be implantable in a human eye that comprises at least a section of a lens capsule, a ciliary muscle and zonules controlled by the ciliary muscle. By way of a special ring that is designed so as to cooperate with the ciliary muscle, linkage arms are formed, each of which is pivotably attached to the optic at a first position on the arm, and is fixed to the said ring at a second position on the arm. The linkage arms are intended to strengthen or enlarge the possible lens movements.

Adaptive lenses spaced apart from one another along the optical axis, in order to improve the accommodation capacity, are described for example in the U.S. Pat. No. 5,275,623. Specifically, the focussing there is achieved by shifting the lens axially in response to the normal contraction and expansion of the ciliary muscle. In the solution according to U.S. Pat. No. 5,275,623 the lens capsule remains present, but at least one additional lens is inserted. After subsequent closure the resulting hollow body, which in the exemplary embodiment mentioned there encloses two axially separated lenses, can be filled after lens implantation with a gas or liquid in order to separate the two lenses by a standard distance.

Such an implantation does not promise much success, because the lens capsule is practically impossible to close at present by surgical means. Hence the arrangement lacks a crucial element for conducting the muscular forces into the implant.

The state of the art as described above furthermore does not make possible any basic surgical adjustments that would allow the intraocular lens implant to be installed at precisely the correct distance from the retina, so as to enable the desired optimal long- and short-distance vision.

The document DE 689 02 614 T2 discloses an accommodating intraocular lens for the human eye that changes its light-refraction characteristics in response to movement of the eye muscle, so as to sharpen the focussing of objects that are at different distances, from the observer's point of view. In this regard a chamber filled with fluid under pressure is provided there, and a supporting vessel is needed to expand the lens capsule far enough to touch the ciliary body. A problematic aspect of the solution according to DE 689 02 614 T2 is the anchoring of the implant in the tender and sensitive lens capsule, which carries a corresponding risk that the capsule will be destroyed before, during or after the implantation.

In the case of the intraocular lens implant according to U.S. Pat. No. 6,217,612 B1 anchoring within the lens capsule is likewise necessary, with all the above-mentioned difficulties during the operation and postoperatively.

According to the teaching of U.S. Pat. No. 4,892,543 a fluid cushion is employed, which is pressed into a convex form by the contour of a rigid lens. This fluid cushion can either act on the ciliary muscle or be inserted into the lens capsule.

In the artificial lens arrangement according to U.S. Pat. No. 4,888,012 a fluid depot is inserted, which controls a lens formed by filling. The light refraction in this case is brought about by the optical properties of the fluid, which means that some substance other than the one naturally present must be employed.

SUMMARY

In view of the preceding considerations, it is the objective of the invention to disclose a further developed accommodative lens implant controlled by the ciliary muscle and consisting of at least one or more lenses disposed on a common optical axis, which is suitable for replacing the natural lens of the eye and which provides the possibility of making an adjustment even after installation so as to produce a natural accommodation, allowing the eye to focus correctly even without corrective spectacles.

The objective of the invention is achieved with a ciliary-muscle-actuated, accommodative lens implant according to the characteristics given in claim 1, while the subordinate claims represent an at least advantageous design and further development.

In accordance with the basic idea of the invention, a first embodiment is based on complete replacement of the original, natural eye lens or lens capsule.

The lens implant in accordance with the invention possesses a flexible, closed implant body, which is transparent in the region of the actual lens and is inserted into and fixed in the sulcus of the posterior eye chamber, or an implant body that is set onto the ciliary muscle so as to make contact over a large area. The implant body comprises at least one lens disposed on the visual axis.

The implant body with the lens or lenses is optionally filled with a fluid, the volume of which can be altered.

The axial position of the lens or, in the case of several lenses, of the resulting lens system can be varied by activation of the ciliary muscles, so as to ensure the desired focussing for the purpose of short- and long-distance vision.

The change in shape of the implant body that is necessary to change the position of the lens therein along the optical axis of the eye is achieved by its fixation to the ciliary muscle and the possibility of contraction but also expansion, depending on the activated ciliary muscle. The anchoring can be brought about, for example, in the sulcus of the posterior chamber.

Now, in order to achieve the desired adjustment of the basic optical position while taking into account the natural situation in the patient concerned, the fluid-filling cavity of the implant body is in communication with a fluid depot, which is preferably situated in the anterior part of the eyeball.

The fluid depot can be filled and emptied, even postoperatively, in order to bring about a basic positioning of the lens or lens system within the eye that can also be corrected later, while taking into account the possibilities and limits of ciliary muscle activity.

For example, by microinjection applied to the fluid depot, liquid can be removed or added with the consequence that the degree of filling, and hence the basic shape of the implant body itself, can be altered or adjusted.

Although in accordance with the invention the implant body is in contact with the ciliary muscle over a large area, this cannot prevent production of aqueous humour, on one hand because of the open structure of the material apposed to the muscle, and on the other hand because it is securely anchored with claws and haptics. In contrast to the state of the art, in which the lens implant is assumed to be anchored in the lens capsule, the prerequisite here is that the capsule itself should be intact and suitable for a corresponding implantation. Even if these prerequisites are fulfilled, a serious problem remains with respect to the time during which the implant remains in use. Most commonly, within a few months after the operation a secondary cataract appears, having been caused by clouding of the remainder of the capsule. The known means of eliminating this at present is a laser treatment in which the occluded parts of the capsule are destroyed. However, the damage to the lens capsule, which occurs by this time at the latest, causes the implant also to become nonfunctional, and in the most problematic case the implant can even migrate out of the capsule.

In the case of an implant according to the invention the lens capsule can of course in principle be left in place, but partial or complete removal is also possible, even postoperatively, without affecting implant function because the implant is directly seated on the ciliary muscle.

DESCRIPTION OF THE DRAWINGS

In the following the invention is explained in greater detail with reference to drawings, wherein.

DETAILED DESCRIPTION

Figure 1:
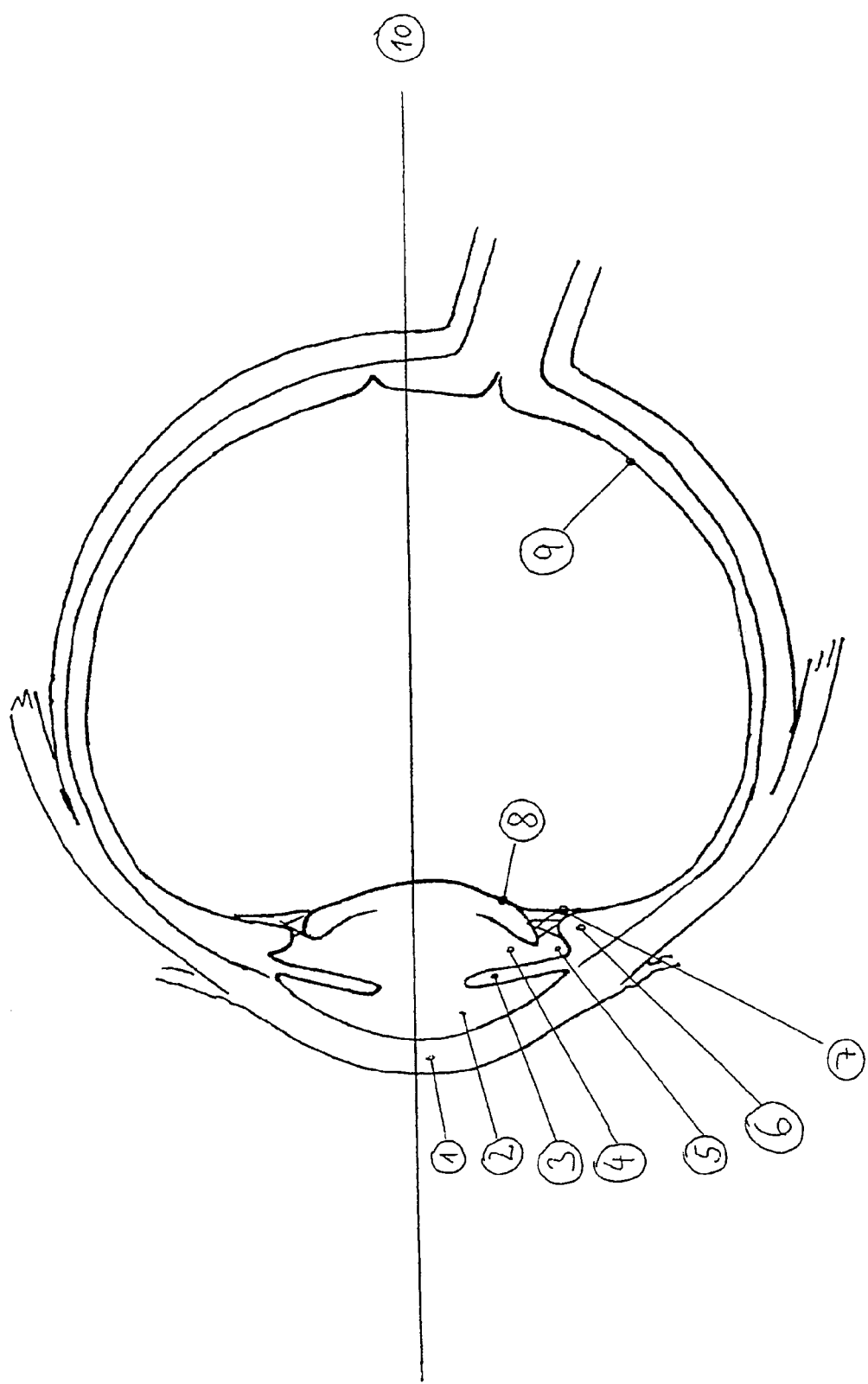
FIG. 1 is a cross-sectional drawing showing the structure in principle of the eye after removal of the lens.

The drawing in FIG. 1 shows the cornea 1 in the anterior region of the eyeball, with anterior optic chamber 2 situated behind it. Reference numeral 3 identifies the iris of the eye.

The visual axis is labelled by the reference numeral 10. The numeral 5 identifies the sulcus between the ciliary muscles and the iris, while 6 indicates the origin of the ciliary muscles and the muscles themselves. The zonule fibers are identified by the numeral 7, the lens capsule by 8, and the retina by 9.

Figure 2:
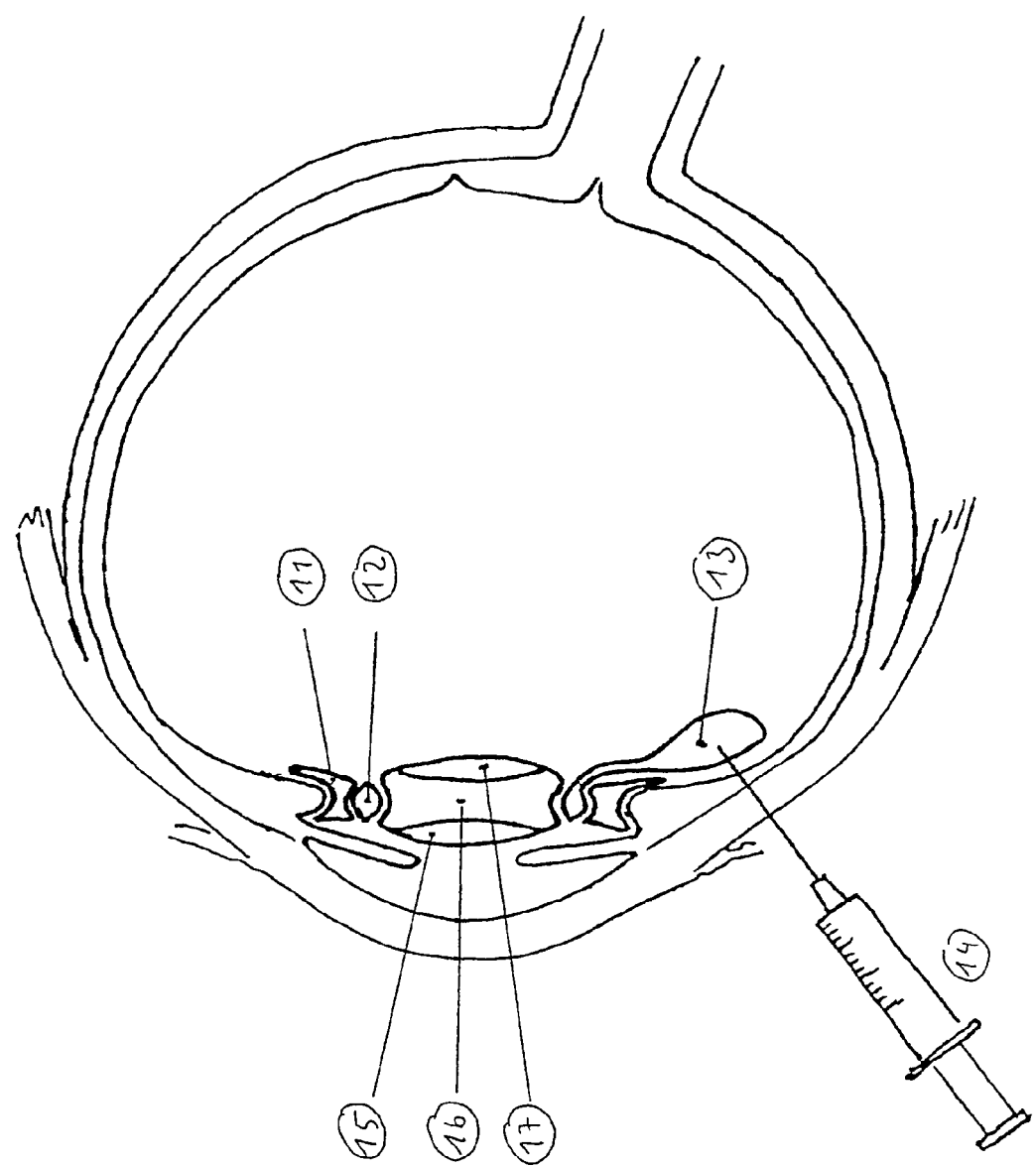
FIG. 2 is a drawing of the eye with implant inserted and relaxed ciliary muscle, for long-distance vision

In the drawing in FIG. 2 a place holder is discernible, namely the intermobile element 11 that fixes the position of the implant, the latter consisting of outer lens 15, fluid-filled cavity 16 and inner lens 17. Between the intermobile element 11 and the implant there is another fluid depot 12 constructed as a ring, which communicates with an external injection chamber 13 so that fluid injection can be carried out by way of, for example, a syringe 14. The lens implant shown in FIG. 2 has been adjusted for long-distance vision, being in a state associated with relaxation of the ciliary muscle. The embodiment shown here is based on a tripartite arrangement with lens system, fluid ring plus external injection chamber for adjustment, and the above-mentioned intermobile element or place holder.

Figure 3:
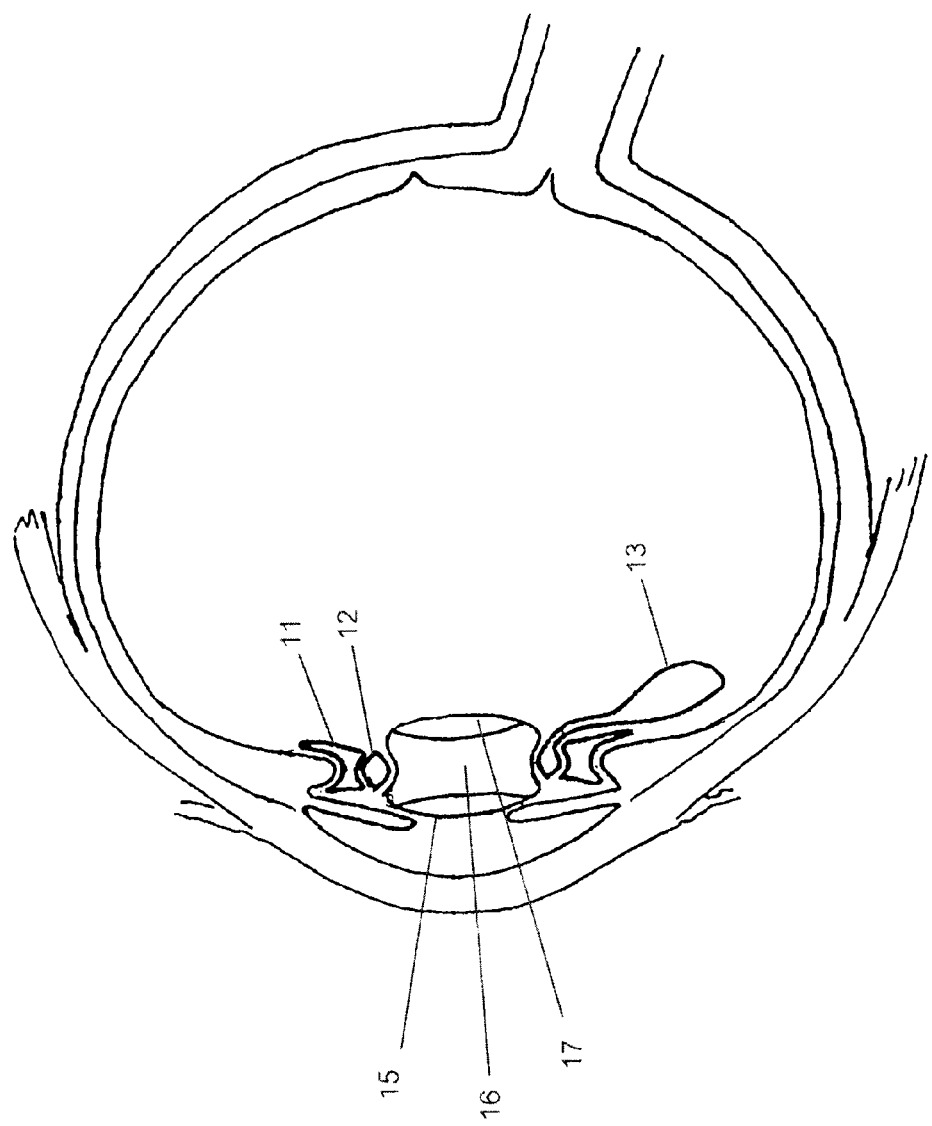
FIG. 3 is a drawing showing the implant when the ciliary muscle is contracted, for short-distance vision.

FIG. 3 shows the lens implant in situ with tensed ciliary muscle, for short-distance vision.

The implant body thus comprises an outer lens 15 and an inner lens 17. The implant body itself forms a cavity 16 that is filled with a fluid, i.e. a liquid or a gas.

By way of the ciliary muscle 6 a force can be exerted on the implant body that causes the distance of the lens or lenses 15, 17 from the retina 9 to change.

The cavity 16 in the implant body, as mentioned, continues to be in communication with the fluid depot 13, which is preferably situated in the front part of the eyeball.

The fluid depot 13 can be filled and emptied postoperatively, so as to produce a basic setting of the position of the lenses or lens system 15, 17 that takes into account the ciliary muscle activity and the patient's own, specific capacity for accommodation; this basic setting can also be subsequently corrected. The degree of filling of the fluid depot 12, 13, and thus indirectly of the cavity 16 in the implant body, can be altered by the desired amount by means of microinjection, by which means the position and the seating of the implant body in the sulcus of the posterior optic chamber can also be optimized.

In another embodiment of the invention it is possible to provide a marker that is visible to the physician and shows the position of the fluid depot, for instance a dot on the anterior lens.

It is likewise possible to employ the implant to correct additional visual defects that ordinarily must be treated with spectacles. Such defects might for example be astigmatism and minor forms of strabismus. Correction of these is made possible because the position of the implant body can be altered in a well-defined manner, e.g. by employing markers, and in principle the possibility exists to construct one lens in the lens system individually before it is connected to the implant body so as to be nonrotatable.

In a preferred embodiment of the invention, to avoid an undesired increase of the internal pressure of the eye, the implant body can be shaped at its outer periphery in such a way that aqueous humour formed by the ciliary processes in the posterior chamber of the eye can be resorbed in the anterior chamber. For this purpose the implant body comprises openings or grooves, or the chamber of the implant body in which the lens system is accommodated is constructed with a reduced diameter, and between ciliary muscle and lens system or implant body there is inserted a place holder or intervening body to serve as intermobile element, which on one hand can transmit the required muscular pressure whereas on the other hand it enables the aqueous humour to flow away. The place holder and the implant body can be made in one piece, i.e. integrally. A multi-part design favours a minimally invasive surgical procedure, because the pieces that must be surgically introduced are smaller.

To improve the anchoring of the implant body with respect to the ciliary sulcus, shaped projections, claws or similar means for force- and/or form-fitting can be provided.

In order to ensure a minimally invasive operation, in another embodiment of the invention it is possible to construct the implant body with lens system so that it is deformable or foldable, in which case the implant body does not acquire its final shape until it is inserted. This shaping can be implemented, for example, by swelling and/or filling with a fluid. Another possible means of reducing its volume during implantation is to remove the fluid partially or completely from the lens implant.

To transmit the ciliary muscle movement in this embodiment an insert or spacer is likewise provided, which serves to fix the lens system in its final position and ensures that the ciliary muscle movement will be transmitted as desired.

The above-mentioned fluid depot for fine adjustment can be designed as an annular tube provided at the outer periphery of the lens system, and in one embodiment is elastic and exerts a restoring force. This annular tube can be connected to a depot-liquid pocket in case relatively large amounts of liquid are needed, also for the purpose of subsequent adjustment. The spacer ring does not acquire its final form until assembled with the fluid depot and the inserted lens system, and consists for example of individual segments which are connected together analogously to a chain with individual links, or are held together by a thread. A ring constructed from a wire spiral is also possible.

In case it is possible to calculate the features of the implant body in advance and construct it accordingly, so that there is no need of adjustment by means of a fluid depot, it becomes possible to make the spacer ring that acts to transmit force and maintain spacing in such a way that the ring itself fixes the lenses of the system adequately in position.

A surgical technique can be described, for example, as follows. Initially the anterior eye chamber is opened a few millimeters wide. The next step is to open the front of the lens capsule so as to remove the damaged lens. The spacer ring, where appropriate in connection with the fluid depot, is folded together and passed through the operative entrance thus created. Now the ring is shifted from the anterior chamber into the posterior chamber of the eye. Through the remainder of the lens capsule with fibre apparatus the ring is independently guided into the sulcus. As it is unfolded, the zonula fibres that insert on the ciliary muscle ring are transected. However, some intact fibres will remain, and these hold the remaining lens capsule. Subsequently the lens system is likewise shifted through the anterior chamber into the posterior chamber. The place holder or spacer ring in this embodiment is so shaped that the lens system is caught in it. The diameter here is preferably smaller than the maximal iris opening.

In summary, the invention creates a possibility for restoring accommodation ability as part of the process of removing an eye's natural lens. Slight visual defects can be treated at the same time.

In connection with the fluid depot it is also possible to carry out postoperative adjustment. The invention is independent of the presence of lens capsule, zonula fibres and vitreous body.

LIST OF REFERENCE NUMERALS

1 Cornea
2 Anterior chamber of eye
3 Iris
4 Posterior chamber of eye
5 Sulcus between ciliary process and iris
6 Ciliary process with ciliary muscle
7 Zonula fibres
8 Lens capsule
9 Retina
10 Visual axis
11 Intermobile element or place holder
12 Fluid depot in annular design
13 External injection chamber
14 Fluid injection means
15 Outer lens
16 Fluid-filled cavity
17 Inner lens

The invention claimed is:

1. An accommodative lens implant, comprising:
an implant body having at least one lens;
a fluid depot; and
an intermobile element having an annular shape and a radially outward surface dimensioned to be directly engaged by a ciliary muscle of an eye, the radially outward surface of the intermobile element is concavely shaped such that the radially outward surface of the intermobile element is able to straddle said ciliary muscle so as to extend from a first side of said ciliary muscle facing an iris of said eye to a second side of said ciliary muscle facing a retina of said eye,
wherein a first side of said fluid depot is configured to be directly engaged by said intermobile element and a second side of said fluid depot opposite to the first side is configured to be directly engaged by said implant body, and
said implant body, said fluid depot and said intermobile element are separate from one another, each of said implant body, said fluid depot and said intermobile element being sequentially and individually implantable in said eye.

2. The accommodative lens implant of claim 1, wherein said intermobile element includes projections.

3. The accommodative lens implant of claim 1, wherein said implant body has at least one flexible wall, said at least one flexible wall and said at least one lens together forming at least part of a closed chamber that is filled with a fluid, and
wherein when said fluid depot is received by said intermobile element and said implant body is received by said fluid depot, such that said at least one flexible wall of the implant body is able to be acted upon by movement of said ciliary muscle via said fluid depot, said implant body being configured such that a muscular force acting on said at least one flexible wall affects a movement of said at least one lens in a direction substantially parallel to an optical axis of said at least one lens.

4. The accommodative lens implant of claim 1, wherein said implant body is configured to swell to an ultimate form.

5. The accommodative lens implant of claim 1, wherein said implant body includes openings or grooves for passage of aqueous humor.

6. The accommodative lens implant of claim 1, wherein said intermobile element is configured to permit passage of aqueous humor.

7. The accommodative lens implant of claim 1, further comprising an injection chamber in fluid connection with said fluid depot.

8. The accommodative lens implant of claim 7, wherein said fluid depot includes said injection chamber.

9. The accommodative lens implant of claim 1, wherein said fluid depot has an annular shape and said implant body has a circular shape.

10. An accommodative lens implant configured to be controlled by a ciliary muscle of an eye, comprising:
an intermobile element including a first exterior side surface and a second exterior side surface, the second exterior side surface located on an opposite side of the intermobile element from the first exterior side surface, the first exterior side surface of the intermobile element is configured to be attached to the ciliary muscle, the first exterior side surface of the intermobile element is concavely shaped such that the first exterior side surface of the intermobile element is able to straddle said ciliary muscle so as to extend from a first side of said ciliary muscle facing an iris of said eye to a second side of said ciliary muscle facing a retina of said eye;
a plurality of lenses made of a biocompatible material and disposed on a common optical axis, at least one lens being a component of a flexible, closed implant body that is transparent in at least one region, is configured to be connected at its outer periphery to the ciliary muscle by the intermobile element, and has a main axis that coincides with a visual axis; and a fluid depot provided continuously between the implant body and the intermobile element, such that an axial position of the plurality of lenses with respect to each other can be altered by movement of the intermobile element, wherein the second exterior side surface of the intermobile element is engaged with a first exterior surface of the fluid depot, and a second exterior surface of the fluid depot is engaged with the implant body, the second exterior surface of the fluid depot being provided on an opposite side of the fluid depot from the first exterior surface of the fluid depot, the fluid depot configured to be filled with fluid, and wherein the intermobile element enables passage of aqueous humor.

11. An accommodative lens implant according to claim 10, wherein the fluid depot has an annular shape and is in communication with a fluid injection chamber that can be filled and emptied postoperatively, so as to bring about a basic setting of a position of at least one of the plurality of lenses in the eye that takes into account ciliary muscle activity and accommodation ability specific to a patient and that can also be corrected.

12. An accommodative lens implant according to claim 10, wherein the implant body includes openings or grooves for the passage of aqueous humor.

13. An accommodative lens implant according to claim 10, wherein the intermobile element is a spacer ring.

14. An accommodative lens implant according to claim 10, wherein the intermobile element has an annular shape and encircles the fluid depot continuously around a circumference of the implant body.

* * * * *